United States Patent [19]

Sandow et al.

[11] Patent Number: 4,941,874
[45] Date of Patent: Jul. 17, 1990

[54] DEVICE FOR THE ADMINISTRATION OF IMPLANTS

[75] Inventors: Jürgen K. Sandow, Königstein/Taunus; Wilfried De Felice, Kelkheim; Horst Pajunk; Heinrich Pajunk, both of Geisingen, all of Fed. Rep. of Germany

[73] Assignee: Hoechst Aktiengesellschaft, Frankfurt am Main, Fed. Rep. of Germany

[21] Appl. No.: 229,957

[22] Filed: Aug. 9, 1988

[30] Foreign Application Priority Data

Aug. 11, 1987 [DE] Fed. Rep. of Germany ....... 3726654
Jan. 26, 1988 [DE] Fed. Rep. of Germany ....... 3802158

[51] Int. Cl.$^5$ ............................................ A61M 36/12
[52] U.S. Cl. ..................................... 604/60; 604/197; 604/218
[58] Field of Search ................... 604/60, 57, 61, 59, 604/197, 263, 218

[56] References Cited
U.S. PATENT DOCUMENTS

| 3,921,632 | 11/1975 | Bardani . | |
|---|---|---|---|
| 4,308,859 | 1/1982 | Child . | |
| 4,344,573 | 8/1982 | De Felice | 604/60 |
| 4,601,699 | 7/1986 | Crain | 604/60 |
| 4,801,263 | 1/1989 | Clark | 604/60 |

FOREIGN PATENT DOCUMENTS

3419876A1 7/1984 Fed. Rep. of Germany .

*Primary Examiner*—Stephen C. Pellegrino
*Attorney, Agent, or Firm*—Finnegan, Henderson, Farabow, Garrett and Dunner

[57] ABSTRACT

The invention relates to a device for the injection of implants, preferably implants "in the form of small rods" (called rods), which are used for the long-term treatment of diseases, whose essential features are the completely transparent construction, especially of the injector body (3), as well as a protecting device which prevents the plunger rod from falling out, and a protective cap (6) for the plunger rod.

11 Claims, 2 Drawing Sheets

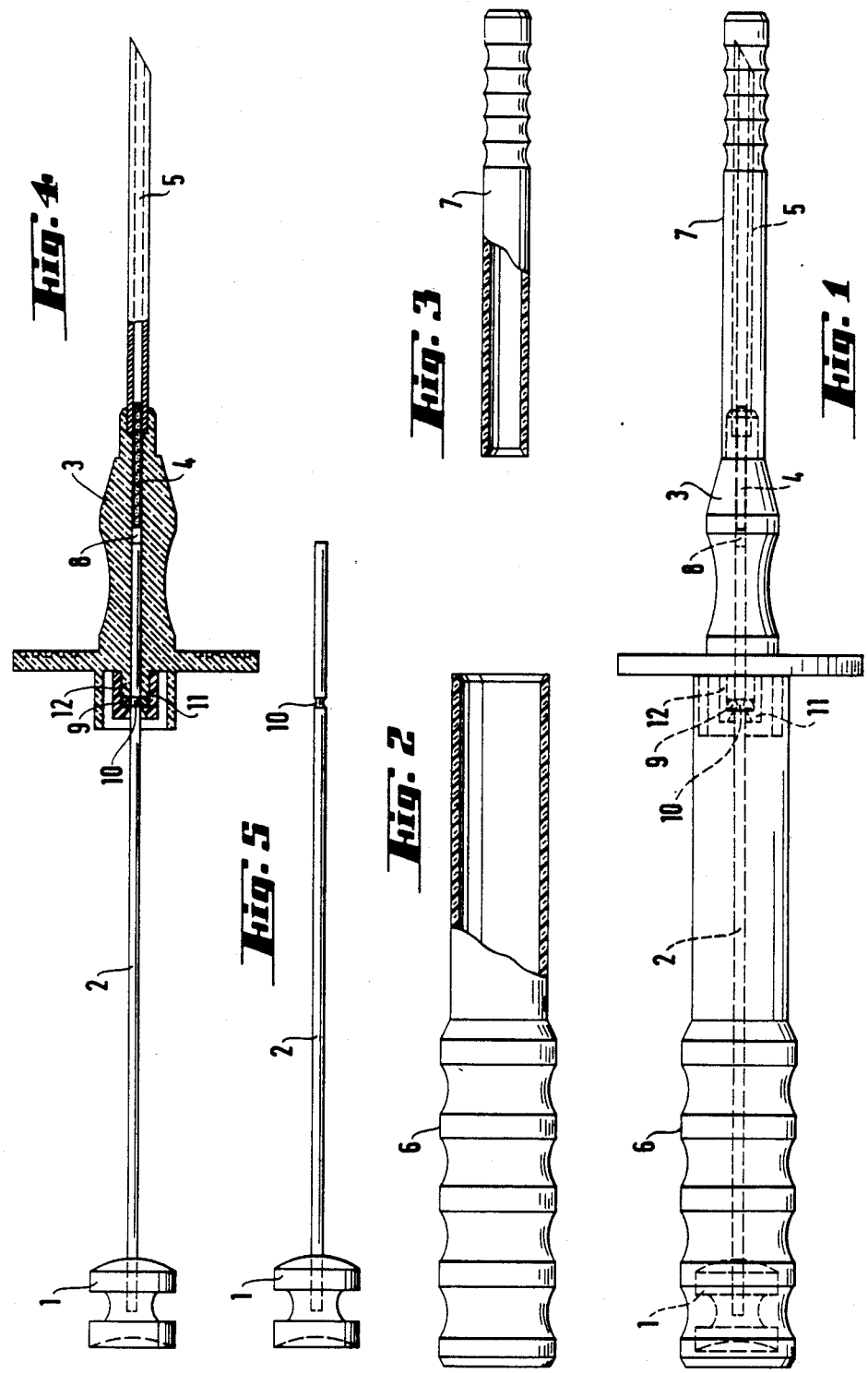

DEVICE FOR THE ADMINISTRATION OF IMPLANTS

BACKGROUND OF THE INVENTION

1. Field of the Invention

The invention relates to a device for the injection of implants, preferably implants in the form of small rods, (called rods), which are used for the long-term treatment of diseases.

2. Description of the Related Art

The administration of such implants has recently acquired importance because there has been the development of plastics which undergo controlled degradation in vivo, and thus release, over a prolong period the active substance which is entrapped in, for example, a matrix or is chemically bonded thereto (active substance depot forms).

It is no longer possible for modern drug therapy to dispense with these delivery forms which combine a controlled rate of release of the active substances with high biocompatability of the depot. Such long-lasting controlled release of active substance is of great current interest because of the increasing importance of chronic diseases and therapeutic policies oriented to the long-term in human and veterinary medicine.

Devices for the administraction of active substance depot implants, which are mostly designed as small cylindrical rods, have already been disclosed. Most of them comprise an active substance container in which the rod is located, and an injection cannula attached thereto and a plunger to introduce the active substance composition into the subcutaneous tissue by being advanced.

German Offenlegungsschrift No. 3,419,876 decribes a mechanically relatively elaborate device for the subcutaneous administration of depot bodies, in which the depot body is located immediately before the pointed cannula orifice. On administration, the cannula is introduced into the subcutaneous tissue. A member which can be displaced is then used to withdraw the needle from the tissue, while a fixed pluger rod, which is in contact with the depot body, ensures that only the cannula is retracted concentrically around depot body and plunger rod, and the depot body remains in the tissue. The depot body is therefore not pushed into the subcutaneous tissue but is "exposed" in the tissue by the hollow cylindrical cannula being withdrawn over it.

The product information on (®) ZOLADEX Depot (ICI) discloses a device for the administration of implants, in which the active substance container contains a transparent central part (window) so that it is possible to see whether a rod is present in the device or not.

However, the injector described by ICI has the following technical disadvantages when used:

(a) Although the entire administration device is packed sterile in a blister pack, once this has been opened the device must be used as rapidly as possible, otherwise sterility is no longer guaranteed. This supposes that the cannula is still provided with a protective cap, but the plunger rod does not remain sterile in the "unpacked" state, which can be a disadvantage if the plunger rod is moved backwards and forwards several times, in which case the sterility of the active substance cylinder can no longer be guaranteed.

(b) There is the risk that during introduction of the cannula into the subcutaneous tissue there will be premature and unintentional actuation of the plunger rod.

These disadvantages are avoided by the design modifications, which are detailed hereinafter, compared with the ICI injector described above.

SUMMARY OF THE INVENTION

Accordingly, the invention provides:

A device for the injection of implants, comprising an active substance container, a cannula and a plunger rod, wherein the cylindrical plunger channel which runs through the active substance container (injector body) contains a flexible O-ring which runs concentrically around the plunger channel and slightly reduces the internal diameter of the cylindrical plunger channel, and wherein the plunger rod has a concentric groove, and wherein the device is additionally provided with a protective cap both for the cannula and for the plunger rod, and wherein at least the active substance container is fabricated from transparent plastic.

BRIEF DESCRIPTION OF THE DRAWINGS

The accompanying drawings, which are incorporated in and constitute a part of the specification, illustraste a presently preferred embodiment of the invention and, together with the general description given above and the detailed description given below, serve to explain the principles of the invention.

FIG. 1 depicts an implantation device in accordance with the present invention;

FIG. 2 depicts a protective cap for the plunger shown in FIG. 1;

FIG. 3 depicts the protective cap for the cannula shown in FIG. 1;

FIG. 4 depicts the implantation device of FIG. 1 with the protective caps removed;

FIG. 5 depicts the plunger shown in FIG. 1; and

DETAILED DESCRIPTION OF THE PREFERRED EMBODIMENT

Figure 6:
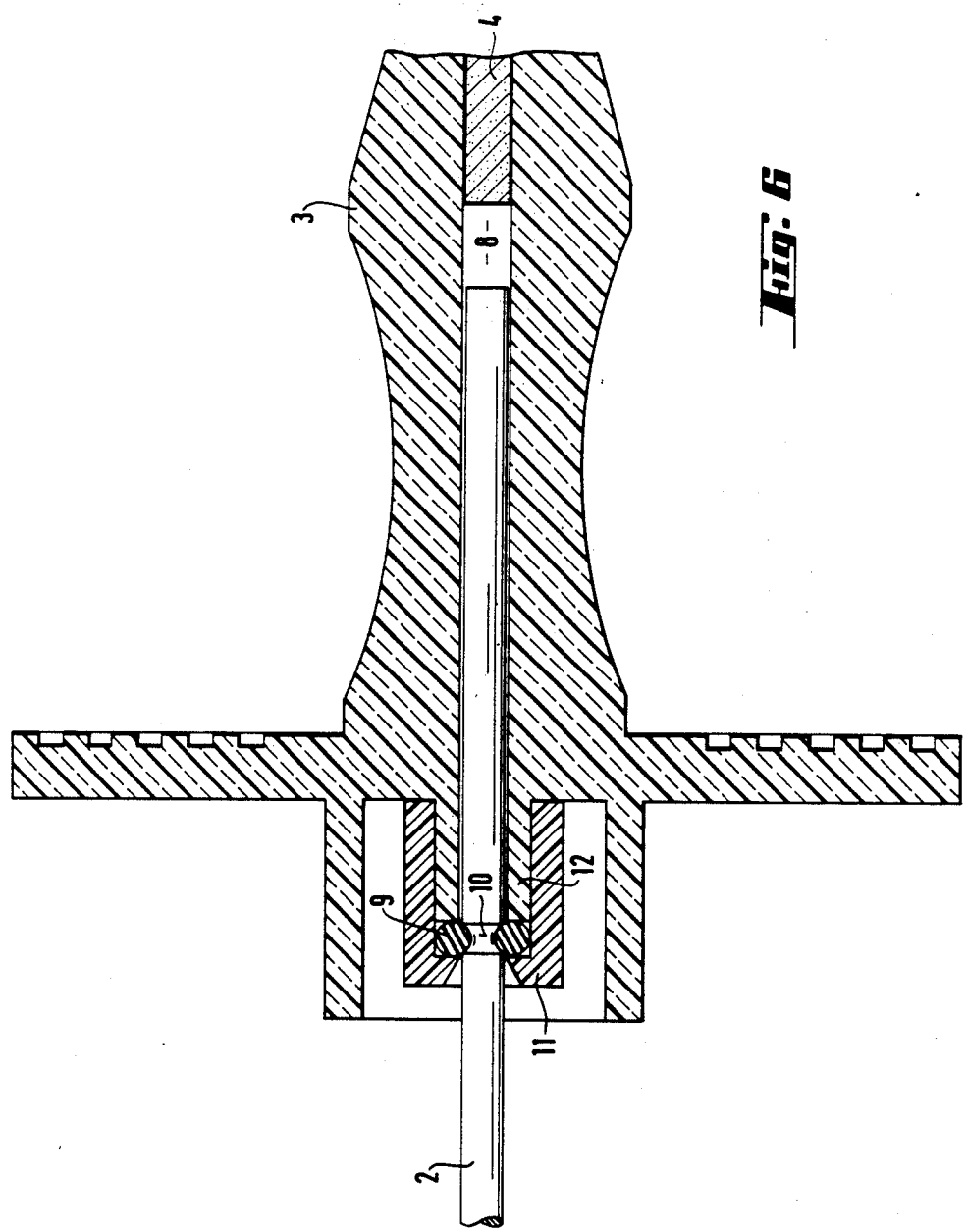
FIG. 6 is an enlarged cross-sectional view of the central area of the implantation device of FIG. 1.

The invention is explained in detail in FIGS. 1-5.

FIG. 4 depicts the device without protective caps for plunger rod and cannula. The active substance cylinder (4) is located in the injector body (3) before the opening or already partly in the cannula (5). The active substance cylinder (4) is advanced into the subcutaneous tissue by means of the plunger rod (2) on which, at its end opposite to the cannula, is the plunger knob (1). The injector body (3) is fabricated in one piece from transparent plastic. The plunger rod and the cannula are fabricated from metal.

FIG. 2 depicts the protective cap (6) for the plunger rod and FIG. 3 depicts the protective cap (7) for the cannula. Both parts (6 and 7) can likewise preferably be fabricated from transparent plastic.

FIG. 1 depicts the complete device with protective caps (6 and 7) in place both for the plunger rod and for the cannula. FIG. 5 shows the plunger rid (2) with the groove (10).

FIG. 6 shows an enlarged detail of the central area of FIG. 4.

According to the invention, the active substance container (3) contains a flexible O-ring (9) which runs concentrically around the plunger channel (8) and slightly reduces the internal diameter of the cylindrical plunger channel. This reduction of the internal diameter is 5–40%, preferably 10–30%, especially 10–20%, of the diameter of the plunger channel. The plunger rod (2) itself has a groove (10) which runs in the form of a ring (concentrically around the plunger rod) and whose depth is preferably 2.5–25%, particularly perferably 5–20%, very particularly preferably 7.5–12.5% of the diameter of the plunger rod.

The remaining developments of the device, such as hollows for gripping the protective caps for the cannula and plunger rod, a grip for the index and middle fingers to rest on, or plunger rod knob, can be varied freely depending on the area of use and should be adjusted to the particular requirements by the expert.

The device is produced by generally customary methods of plastic processing.

The introduction of the O-ring (9) concentrically into the plunger channel (8) of the active substance container (3) can be carried out, for example, by placing the O-ring on the connector (12) projecting beyond the active substance container, and placing over the O-ring and the connector a cap (11) which, for example, is clipped or bonded to the connector.

Suitable plastics for the device according to the invention are those which are non-toxic and can be welded and can be sterilized, and in particular, are insensitive to sterilization using gamma rays. In addition, the plastic which is used must not react with any constituent of the implants (rods) used. Preferably used are polyamides or polycarbonates, especially polycarbonates of 4,4′-dihydroxydiphenylalkanes, such as polycarbonates of 2,4-di(4-hydroxyphenyl)propane ((®) Makrolon, Bayer). The flexible O-ring is preferably composed of polytetrafluoroethylene (PTFE) of silicone. The essential features of the device are:

(a) the completely transparent construction in one piece, especially of the injector body, (b) the protective cap for the plunger rod, and (c) the protecting device which prevents the plunger rod from falling out.

The completely transparent construction, especially of the injector body, means that it is possible for the user to check at any time the presence and condition of the implant, as well as the function of the device during the implantation process.

The flexible O-ring which is arranged concentrically around the plunger channel ensures, in conjunction with the groove in the plunger rod, that the plunger rod does not inadvertently fall out of the active substance container or is not withdrawn from the active substance container at the same time as the protective cap for the plunger rod is removed. The ring engages to a certain extent in the groove so that further inadvertent withdrawal of the plunger rod is avoided.

The protective cap for the plunger rod primarily serves to secure the plunger during the injection, in order to avoid inadvertent actuation of the plunger. However, it additionally maintains the sterility of the part of the device which it covers, so that the device according to the invention remains sterile even in the "unpacked state" (see FIG. 4).

The implantation device can easily be operated by the user with one hand, in compliance with the practical requirements of treatment. For this purpose, firstly the protective cap for the cannula is removed from the device as depicted in FIG. 4. Subsequently the cannula is introduced into the cutaneous tissue. Only now is the protective cap (6) of the plunger rod removed and— where appropriate after partial retraction of the cannula from the tissue—the implant is placed in the tissue by pushing the plunger rod completely through.

The area of use relates to subcutaneous or intramuscular injection of pharmaceutical-containing rods composed of biodegradable polymeric material having the dimensions 0.6 mm to 3 mm in diameter and a length of 0.5 to 30 mm. Use is also possible by introducing the implants into joints or body cavities. The body cavities must be accessible to the cannula and allow the active substance to be transported away. Examples which may be mentioned here are: frontal sinus, thoracic cavity, abdominal cavity or cysts or cavities produced by inflammations or other pathological processes.

We claim:

1. A device for the injection of implants comprising:
an active substance container fabricated from transparent plastic, having a first end opening, a second end opening, and a cylindrical plunger channel extending between and connecting said first and second end openings, said cylindrical plunger channel including a flexible O-ring for reducing the internal diameter of said channel at a predetermined location;
a cannula extending from said first end openings;
a plunger rod movably disposed in said channel and extending from said second end opening, said rod having a concentric groove therein for receiving said O-ring;
a first protective cap for covering said cannula; and
a second protective cap for covering said plunger rod.

2. A device as claimed in claim 1, wherein all the parts, except the plunger rod and the cannula, are fabricated from transparent plastic.

3. A device as claimed in claim 1, wherein the flexible O-ring is fabricated from polytetafluoroethylene or silicone.

4. A device as claimed in claim 1, wherein the slighe reduction of the internal diameter of the plunger channel by the O-ring is 5–40% of the diameter of the plunger channel.

5. A device as claimed in claim 1, wherein the groove in the plunger rod has a depth of 2.5–25% of the diameter of the plunger rod.

6. A device as claimed in claim 1, wherein the implants have the form of small cylindrical rods.

7. The device as claimed in claim 1 including an active substance depot disposed in the active substance container.

8. A device for injection of implants, comprising:
an active substance container having a first end opening, a second end opening, and a cylindrical plunger channel extending between and connecting said first and second end openings, said cylindrical plunger channel including a flexible O-ring for reducing the internal diameter of said channel at a pre-determined location;
a cannula extending from said first end opening;
a plunger rod movably disposed in said channel and extending from said second end opening, said rod having a concentric groove therein for receiving said O-ring; and
a protective cap of covering said plunger rod to prevent inadvertent movement of said plunger rod.

9. A device as claimed in claim 8 wherein said active substance container is made of transparent plastic.

10. A device as claimed in claim 8 further comprising a protective cap for covering said cannula.

11. A device as claimed in claim 8 further comprising a connector cap disposed on said second opening, said flexible O-ring being disposed between said connector cap and said second opening.

* * * * *